US006957108B2

(12) United States Patent
Turner et al.

(10) Patent No.: US 6,957,108 B2
(45) Date of Patent: Oct. 18, 2005

(54) INVASIVE MICROWAVE ANTENNA ARRAY FOR HYPERTHERMIA AND BRACHYTHERAPY

(75) Inventors: Paul F. Turner, Bountiful, UT (US); Mark Hagmann, North Salt Lake, UT (US); Thomas Youd, Salt Lake City, UT (US)

(73) Assignee: BSD Medical Corporation, Salt Lake City, UT (US)

( * ) Notice: Subject to any disclaimer, the term of this patent is extended or adjusted under 35 U.S.C. 154(b) by 153 days.

(21) Appl. No.: 10/453,018

(22) Filed: Jun. 2, 2003

(65) Prior Publication Data

US 2004/0243200 A1 Dec. 2, 2004

(51) Int. Cl.[7] .................................................. A61F 2/00
(52) U.S. Cl. .......................................... 607/101; 600/2
(58) Field of Search ........................... 607/96, 101–102; 600/2; 606/133

(56) References Cited

U.S. PATENT DOCUMENTS

| | | | | | |
|---|---|---|---|---|---|
| 4,204,549 | A | * | 5/1980 | Paglione | ...................... 607/102 |
| 4,292,960 | A | * | 10/1981 | Paglione | ........................ 600/2 |
| 4,448,198 | A | | 5/1984 | Turner | |
| 4,712,559 | A | | 12/1987 | Turner | |
| 4,763,671 | A | * | 8/1988 | Goffinet | ........................ 600/2 |
| 4,860,752 | A | | 8/1989 | Turner | |
| 5,106,360 | A | * | 4/1992 | Ishiwara et al. | ................ 600/2 |
| 5,531,662 | A | * | 7/1996 | Carr | ............................... 600/2 |

OTHER PUBLICATIONS

Overgaard, Simultaneous and Sequential Hyperthermia and Radiation Treatment of an Experimental Tumor and Its Surrounding Normal Tissue in Vivo, 1980, Int.J. Radiation. Onc. Biol. Phys. vol. 6, pp. 1507–1517.

Overgaard, The Future of Hyperthermic Oncology, Proceedings of the 6th International Congress on Hyperthermia Oncology, vol. 2, 1992, pp. 87–92.

Stone and Dewey, Biologic Basis and Clinical Potential of Local–Regional Hyperthermia, Radiation Oncology, vol. 2 Editor Phillips and Wara, 1987 Raven Press, NY., pp. 1–33.

Steeves et al., Thermoradiotherapy of Intraocular Tumors in an Animal Model: Concurrent vs. Sequential Brachytherapy and Ferromagnetic Hyperthermia, 1995, Int. J. of Radiation Oncology, Biology, Physics, vol. 33 (3), pp. 659–662.

Turner, Interstitial Equal–Phase Arrays for EM Hyperthermia, IEEE Trans. MTT–34(5),May 1986,572–578.

(Continued)

Primary Examiner—Roy D. Gibson
(74) Attorney, Agent, or Firm—Robert R. Mallinckrodt

(57) ABSTRACT

A microwave hyperthermia apparatus that can be inserted into the body which includes a hollow central tube for the insertion of radioactive therapy sources. The use of a coaxial transmission line impedance transformation along the insertable portion of the coaxial cable enables a reduction in the characteristic impedance by increasing the outer diameter of the inner coaxial conductor so that the center conductor can be a metal tube. If the ratio of the outer coaxial conductor diameter vs. the inner coaxial conductor is decreased, the characteristic impedance of the transmission line is lowered. This enables the inner conductor diameter to increase sufficiently to make the central hollow opening large enough to receive standard radioactive sources therein. This provides for a good impedance match that improves microwave energy efficiency while at the same time permitting a large hollow center opening. The combination of the microwave antenna device and brachytherapy sources provides for enhanced effectiveness when the two treatments are delivered simultaneously or in close time proximity to each other.

27 Claims, 4 Drawing Sheets

OTHER PUBLICATIONS

Meyerson et al. Simultaneous superficial hyperthermia and external radiotherapy: Report of thermal dosimetry and tolerance to treatment, Int. J. of Hyperthermia 1999; 15(4):251–266.

Goss et al., Abstract, An Examination of Simultaneous Multi–Frequency Planar Array Ultrasound Applicators for Hyperthermia, Proc., 15th Annual Meeting of the North American Hyperthermia Society, Apr. 16, 1995, p. 107.

Hand, Microwave Techniques for Interstitial Hyperthermia, *Interstitial and Intracavitary Thermoradiotherapy*, Chapter 6, Springer—Verlag, 1993, NY,pp. 43–48.

Diederich et al., Combination of transurethral and interstitial ultrasound applicators for high–temperature prostate thermal therapy, Int. J. of Hyperthermia, 2000, 16(5),385–403.

Leybovich et al., A modified technique for RF–LCF interstitital hyperthermia, Int. J. of Hyperthermia, 2000,16(5), 405–413.

Kim et al., Effect of simultaneous pulsed hyperthermia and pulsed radiation treatment on survival of SiHa cells, Int. J. of Hyperthermia, 1998, 14(6),573–581.

Diederich et al. Direct–coupled interstitial ultrasound applicators for simultaneous thermobrachytherapy: a feasibility study, Int. J. of Hyperthermia 12(3):401–419, 1996.

Straube et al., Dosimetry and techniques for simultaneous hyperthermia and external beam radiation therapy, Int. J. of Hyperthermia, 2001, 17(1),48–62.

Seegenschmiedt et al., Iridium–192 brachytherapy plus interstitial microwave hyperthermia in the treatment of head & neck tumours, 1993, SELECTRON Brachytherapy Journal,7(1),21–33.

Mechling et al., A theoretical comparison of the temperature distributions produced by three interstitial hyperthermia systems, Int. J. Radiation Oncology Biology Physics 1986, vol. 12 2137–2149.

Kapp et al., Interstitial hyperthermia and high dose rate brachytherapy in the treatment of anal cancer: a phase I/II study, Int. J. of Radiation Oncology, Biology, Physics, 1994, vol. 28, 189–199.

Petrovich et al., Interstitial microwave hyperthermia combined with iridium–192 radiotherapy for recurrent tumors, Am. J. Clinical Oncology (CCT), 1989,12(3),264–268.

Linares et al., Interstitial Hyperthermia and brachytherapy: A Preliminary Report, Endocurie, Hypertherm, Oncology Journal 1986, vol. 2,pp.S39–S44.

Kaatee et al., A 27 MHz current source interstitial hyperthermia system for small animals, Int. J. of Hyperthermia, 1995,11(6),785–796.

Corry et al., Hyperthermia with chronically implanted electrodes for tumors in the thorax, abdomen and pelvis, Proceedings of the 5th International Symposium on Hyperthermia Oncology, 1988, vol. 2, 658–661.

Corry et al., Thermobrachytherapy: Requirements for the Future, *Interstitial and Intracavitary Thermoradiotherapy*, Chapter 41, Springer—Verlag, 1993, NY,pp. 373–379.

Kasai et al., Improved reliability of repetitive RF interstitial heating in combination with brachytherapy: the effective use of water, Int. J. of Hyperthermia, 2001, 17(2),160–171.

Goldson et al., Simultaneous Intraoperative Radiation Therapy and Intraoperative Interstitital Hyperthermia for Unresectable Adenocarcinoma of the Pancreas, Endocurie, Hypertherm, Oncology Journal,ISSN 8756–1687, Oct. 1987,pp. 201–207.

Sneed, et al., *Survival Benefit of Hyperthermia in a Prospective Randomized Trial of Brachytherapy Boost ± Hyperthermia for Glioblastoma Multiforme*, 1998, Int. J. of Radiation Oncology, Biology, Physics, vol. 40 (2), pp. 287–295.

Cumberlin et al., *New Directions In Brachytherapy*, 2002, Int. J. of Radiation Oncology, Biology, Physics, vol. 53, No. 1, pp. 6–11.

* cited by examiner

INVASIVE MICROWAVE ANTENNA ARRAY FOR HYPERTHERMIA AND BRACHYTHERAPY

BACKGROUND OF THE INVENTION

1. Field

The invention is in the field of methods and apparatus for administering hyperthermia treatments and brachytherapy treatments.

2. State of the Art

As is generally known, heating to temperatures elevated above a normal cell temperature causes death or necrosis of living tissue. Further, the death rate of such heated tissue is a function of both the temperature to which it is heated and the duration for which the tissue is held at such temperatures.

It is also well known that the elevation of temperature of living tissue can be produced with electromagnetic energy at frequencies greater than about 10 kHz. Microwave frequencies that are above 300 MHz have generally been used for this purpose with a preference for 915 MHz, as approved by the Federal Communications Commission for medical devices.

It has been reported that some types of malignant cells may be necrotized by heating them to a temperature which is slightly below the temperature injurious to most normal cells. In addition, some types of malignant cells may be selectively heated and necrosed by hyperthermia or thermal therapy techniques because masses of these malignant cells typically have considerably poorer blood flow and thus poorer heat dissipation properties than does the surrounding normal tissue. As a result, when normal tissue containing such malignant masses is heated by EMR (electromagnetic radiation), the resultant temperature of the malignant mass may be substantially above that of the surrounding healthy tissue.

It has been determined that most malignant cells have significant damage by heat alone when heated at temperatures over 43° C. for at least 30 minutes. It has also been shown that for every degree increase in temperature above 43° C., the effective thermal dose and tissue damage is doubled. Thus, the same thermal dose would be expected at temperatures of 43° C., 44° C., and 45° C. for respective treatment times of 60, 30, and 15 minutes.

It has also been shown that the combined use of radiation therapy with higher temperatures greatly increases the damage to cells. This increased cell damage is decreased as the heating treatment and the radiation treatment are separated in time. It has been shown by Overgaard that the tissue damage to cancerous tumors is boosted by a factor of 2.5 for a standard radiation dose by adding hyperthermia at the same time.

For over 25 years, hyperthermia and radiation have been studied both clinically and in animal tumor models. Everyone has recognized that there is a benefit for combining hyperthermia and radiation, but the problem has always been how one could best do it. Biological and animal studies continually confirm that simultaneous treatment with the two methods would produce greater cell kill and damage to the tumor. However, the devices and methods of these two modalities were not very compatible for simultaneous treatments. Also, the exposure of normal tissues to the same combined doses increased the damage to the normal tissue. Over the years nearly all the clinical studies of radiation plus hyperthermia were conducted using standard radiation therapy scheduling where about 2 Gy of radiation was applied 5 times per week for about 6 weeks for a total dose of 60 Gy. This is generally considered a rather high dose for external beam radiation. Yet, it was common for hyperthermia to only be applied once or twice per week. This was largely because of biological concerns that thermal tolerance would develop in the tissues making the tumor less damaged by the same hyperthermia treatment if it was not separated by at least 48 hours from the previous hyperthermia treatment. Also it was common for the radiation therapy to proceed hyperthermia due to scheduling problems in radiation departments. There was usually about 30 to 60 minutes from the radiation treatment until the patient was actually at therapeutic temperatures. The fact that normally only about $1/5^{th}$ of the radiation treatments had a concomitant hyperthermia treatment meant that a rather small portion of these radiation treatments would have any resulting enhancement of the tumor damage. There was also direct tumor damage from the heat itself that would typically cause rapid initial reduction of the tumor.

Overgaard Studies

Much of the early pioneering basis for this combination originated from the research of Overgaard. In 1980, Overgaard published a study using nude mice to determine the affects of hyperthermia and radiation time sequencing with various temperatures and treatment times. (Overgaard, Simultaneous and Sequential Hyperthermia and Radiation Treatment of an Experimental Tumor and Its Surrounding Normal Tissue in Vivo, 1980, Int. J. Radiation. Onc. Biol. Phys., Vol 6, pp. 1507–1517). In this work, Overgaard used a new term called the Thermal Enhancement Ratio (TER). This is defined as the radiation dose that is required to obtain a given end point with radiation alone relative to the radiation dose needed for the same effect with combined heat and radiation. Evaluation of the TER was primarily based upon the radiation dose which indicates local control at 120 days after treatment in 50% of the animals. When the presence of the tumor was not detectable, they used histopathological studies to determine the performance. In this study, the basis of thermal dose was established. At the time, they were trying to determine if scheduling of the radiation and hyperthermia treatment might be able to increase the effect on the tumor more than the affect to normal tissue exposed to the same treatment doses. This study did not show much of a difference between normal and tumor damage. However, it did show that there were significant benefits to combining the radiation and the hyperthermia at the same time if the application of the dose could be avoided on normal tissues.

Overgaard showed that one hour of heating at 43.5° C., could increase the TER to 4.9 for a 60 minute heating, 2.54 for a 30 minute heating, and 2.37 for a 15 minute heating. This means that at 43.5° C. for 15 minutes delivered simultaneously with a radiation dose of 30 GY would be equivalent to a radiation dose of 71 Gy. Yet, the long term affects of radiation would be predicted to only be that of the 30 Gy. A factor of over 2 is a tremendously powerful enhancement to boost effectiveness and potentially treatment durability.

The Overgaard mouse studies also show that when the hyperthermia was 24 hours before or after the radiation treatment the TER was 1.5. This implies that there was additional benefit even when there was a 24-hour time separation between hyperthermia and radiation. This should be also taken into account when evaluating the enhancement affects.

In this work, it was also shown that for a heat treatment to follow a radiation treatment by about 60 minutes, the TER would drop to 2.06, which is 86% of the value for simultaneous treatment.

Review of Stone and Dewey Studies in Vitro CHO Cells

The published in vitro studies by Dewey, (Stone and Dewey, Biologic Basis and Clinical Potential of Local-Regional Hyperthermia, *Radiation Oncology, Vol.* 2, Editor Phillips and Wara, 1987 Raven Press, NY., pg. 1–33), showed that heat to 42.5° C. for 60 minutes when combined with a single radiation treatment of 5 Gy produced a cell survival of only about $1.4 \times 10^{-4}$ for cells with a pH of 6.7. This effect was observed even when hyperthermia was applied for up to 180 minutes before radiation. This same benefit was not seen for cells with pH of 7.45 when significant time separated the hyperthermia and the radiation treatment. However, when the hyperthermia and radiation were simultaneous, the survival of the high pH cells ($2 \times 10^{-4}$) almost reached that of the low pH cells. When there was a 60-minute separation between the hyperthermia and radiation the survival of the high pH cells increased to about $1.5 \times 10^{-3}$. So about 10 times more of the high pH cells survived with a 60-minute separation as compared with simultaneous treatments. This demonstrates the significant benefit of simultaneous use of hyperthermia and radiation.

In vivo studies of Dewey showed that by heating to 42.5° C. for 60 minutes, when combined with simultaneous radiation, the TER reached 2.5. This changed to about 1.5 to 1.8 when there was a 60 minutes separation between the two treatment modes.

Review of Steeves Brachytherapy and Hyperthermia

Steeves et al. published results of the timing sequencing of hyperthermia and brachytherapy on intraocular tumors in 45 rabbit eye melanomas. (Steeves et.al. *Thermoradiotherapy of Intraocular Tumors in an Animal Model: Concurrent vs. Sequential Brachytherapy and Ferromagnetic Hyperthermia*, 1995, Int. J. of Radiation Oncology, Biology, Physics, Vol. 33 (3), pp. 659–662.). The study uses a single radiation and hyperthermia treatment. The plague-scleral interface was heated to 46–47° C. for one hour. Treatments with simultaneous heating and radiation were compared to these when hyperthermia was given 1 hour after radiation. With a follow-up of 4 to 10 weeks, they found that simultaneous hyperthermia and radiation therapy produced a 4.4 thermal enhancement ratio as compared to only a 1.4 value for the sequential treatments.

Review of Hyperthermia Plus Radiation Clinical Practices

There have been many Phase I, II, and III clinical studies that have been reported in the literature that combined radiation with hyperthermia. These studies almost always concluded that significant benefits resulted from the combination for both short and long term. All of these studies have been performed using between 3 and 10 hyperthermia treatments combined with typically 25 to 30 external beam radiation treatments.

Dr. Penny Sneed's study on Glioblastoma (Sneed, et al., *Survival Benefit of Hyperthermia in a Prospective Randomized Trial of Brachytherapy Boost ±Hyperthermia for Glioblastoma Multiforme*, 1998, Int. J. of Radiation Oncology, Biology, Physics, Vol. 40 (2), pp. 287–295) applied brachytherapy for 5 days, with hyperthermia for 30 minutes prior to and after the brachytherapy. At the rate of between 0.4 to 0.6 Gy/hr, most of the radiation dose would not be significantly enhanced by the hyperthermia as a result of hyperthermic radiosensitization. However, there may have been additional benefits from reoxygenation.

Expectations for Past Studies from Literature

A conclusion that can be drawn is that relatively few radiation treatments performed with hyperthermia treatment were enhanced by the addition of hyperthermia because most of the radiation was not performed in close time relationship with the hyperthermia. On average, it is estimated that about 5 hyperthermia treatments would be used over a typical radiation treatment regime of about 30 treatments in about 6 weeks. This means that only $\frac{1}{5}^{th}$ of the radiation treatments were significantly complimented by the hyperthermia.

Implications for Brachytherapy Plus MW Interstitial Hyperthermia

The possibility exists to provide simultaneous treatment with hyperthermia and radiation when high dose rate (HDR) is used and common treatment delivery devices are used. Such has motivated the work of Martinez. If each of the brachytherapy treatments using HDR were combined with simultaneous hyperthermia and if the hyperthermia treatment was to raise 50% of the tumor volume to a temperature over 43.5° C. for 30 or 60 minutes, the predicted TER from Overgaard would be between 2.5 to 5. However, a time delay of about 15 minutes between the hyperthermia and the radiation would drop this by a factor of 0.92. The results for a 50 Gy plus hyperthermia treatment would then be equivalent to a radiation dose of 115 to 230 Gy. This higher dose effect would clearly be in the portions of the tumor that more easily would reach the temperature of 43.5° C. or above. This would be the necrotic region with lower blood flow that tend to be significantly radiation resistant. Current experience has led to the understanding that the addition of hyperthermia to standard radiation therapy does not increase short term or long-term toxicity or morbidity. There has however been an increased incidence of superficial blisters or burns of about 3 to 5%. It should be noted that for superficial hyperthermia treatment temperatures within 50% of the tumor would generally not exceed 42° C. due to patient discomfort or pain. Interstitial treatments generally are not as limited by patient pain since the energy is delivered more directly within the tumor. In the Sneed study, analysis of temperatures showed that 50% of the tumor had an equivalent treatment of 43° C. for a total of 75 minutes, while normal tissue temperatures were not allowed to exceed 44° C. The tumor was not allowed to exceed 50° C. This showed the clinical feasibility of utilizing MW Interstitial treatments to reach temperatures of 43 to 43.5° C.

Discussion

Since such impressive results have been observed with the combination of hyperthermia and radiation even when only a small number of radiation treatments are combined with the heat, it is clear that if simultaneous or near simultaneous treatments are delivered with MW Interstitial treatment where the local tumor temperatures can reach a higher level and most of the radiation dose can be significantly enhanced by the hyperthermia there could be significant future benefits. The MW Interstitial combination with HDR appears to offer a boost of between 2 to 5 depending on how it is implemented with the HDR and the duration of heating between 30 to 60 minutes. Such a significant enhancement represents major end results for response durability, radiation dose reduction, treatment efficiency, reduction or elimination of external beam treatment (in some cases) and reduction of patient toxicity.

Overgaard summarized in a published article in 1992 regarding the Future of Hyperthermia Oncology (Overgaard, The Future of Hyperthermic Oncology, Proceedings of the $6^{th}$ International Congress on Hyperthermia Oncology, Volume 2, 1992, pp. 87–92) the following:

> So far most of the results of the combined treatment have utilized the cytotoxic effect of hyperthermia which results in a heat-destruction of radioresistant (hypoxic) tumor cells in solid tumors. In addition to that we have the radiosensitizing effect, which yields a very prominent (temperature and treatment time dependent) enhancement of the radiation damage in normal tissues and tumors. . . . Until now, we have assumed that the therapeutic limitation is the normal tissue tolerance and that a selective heating or radiation treatment of a tumor without involving the surrounding normal tissue will be too heavy a task if the modalities should be applied simultaneously. This concept should be reevaluated since application of hyperthermia together with a boost of radiotherapy is likely to yield a very substantial enhancement, which may have significant implications for the tumor control probability. . . . If hyperthermia should have a meaningful place in curative radiotherapy, we should give maximum priority to further exploration of the hyperthermic radiosensitization and develop our heating techniques accordingly. Both technically, biologically, and clinically should this treatment principle be given the utmost priority in the future research.

Overgaard further emphasized that Interstitial heating and radiation methods open the possibilities to accomplish this enhancement. If there is an hyperthermia enhancement of 2 a high dose 70 Gy radiation treatment could be reduced to 35 Gy for the same tumor result with much lower problems for the patient. The 35 Gy is in the range permitting recurrent radiation treatments after prior radiation failure, so it is also quite suitable for recurrent disease as well as primary.

The facts strongly supporting a simultaneous or close time relationship between radiation therapy and hyperthermia for maximizing the thermal enhancement ratio between radiation and hyperthermia indicate the need for a device to enable a shorter time between radiation and hyperthermia and the possibility of simultaneous treatments.

SUMMARY OF INVENTION

According to the invention, a device which uses the same catheters for brachytherapy and for hyperthermia permits short sequences between radiation and hyperthermia and the possibility of simultaneous brachytherapy and hyperthermia treatments. The time of set-up of the hyperthermia treatment may be similar to the time to set-up the brachytherapy treatment. Each takes about 15 to 30 minutes to set-up. However it also takes about 10 minutes to comfortably get the patient up to treatment temperatures. This additional factor suggests that it may be better to start the hyperthermia first if they must be sequenced. This also then provides the enhancement to the oxygenation of the tumor due to increases in tumor blood flow due to vasodilation.

The device of the invention provides a special microwave interstitial antenna applicator with a hollow center conductor which provides a hollow core. This hollow core is large enough to permit insertion of a standard 0.9 mm brachytherapy source of the HDR treatment systems. This enables a clinician to insert this special applicator/catheter into the patient to permit both radiation therapy and hyperthermia to be delivered by the same inserted device. Several of these devices are typically inserted in a parallel inserted array with spacing between insertions typically about 1 to 1.5 cm. The microwave power connections typically would attach to the side of the device permitting the brachytherapy connection tube to attach to the end of the hollow central tube. The standard brachytherapy equipment includes a metal wire that is attached to the radiation source. However, this prevents simultaneous hyperthermia and brachytherapy treatments since the metal wire and radiation source should not be inserted into the active MW power field during hyperthermia treatment because doing so would permit MW power to be directed into the brachytherapy equipment possibly causing malfunction. In addition, the metal wire of the brachytherapy equipment would disturb the distribution of MW heating.

The challenges to develop such a microwave antenna applicator require that the heating pattern from the antenna be well confined to the tip region of the antenna for a length of about 2 to 6 cm. The energy delivered to the antenna must also be efficiently provided to decrease reflected power from the antenna back to the generator. Such reflected power can alter both the power level and the relative phase of the forward power to be transmitted from the antenna. The power and relative phase are critical in the overall heating pattern when used in a phased array of interstitial antennas. It is also critical to keep the outer diameter of the inserted applicator small enough to be safe and compatible with standard brachytherapy techniques. It is common to use interstitial catheters that are the size of 6 French in diameter (2.0 mm). So there is a requirement to create a hollow center conductor that will accept insertion of the 0.9 mm radiation source with an outer size no bigger than 2.0 mm as the preferred maximum size. Typical sizes of available metal tubing would permit the center coaxial conductor to have a center hollow diameter 0.927 mm to 0.978 mm and an outer diameter of between 1.067 mm to 1.092 mm (1.079 mm average). The standard size of the outer coaxial conductor tube is an outer diameter between 1.816 mm to 1.842 mm and an inner diameter between 1.753 mm to 1.778 mm (1.766 mm average). Using the average specified outer diameter of the center conductor and the average specified diameter of the inner diameter of the outer conductor, the estimated characteristic impedance would be 21 ohms for Teflon dielectric. This 21 ohm impedance would create an impedance mismatch that would reflect about 17% of the incident power at the junction from a standard 50 ohm coaxial cable to the 21 ohm coaxial applicator body. There would be about 83% of the forward power continuing to be directed to the tip of the antenna. It has been experimentally determined that a copper or gold plated center conductor with a stainless steel outer conductor would have about −0.92 dB power loss in a 30 cm long tubular coaxial section with a Teflon dielectric between these two conductors. The reflection that occurs at the transition between the 50 ohm cable and the 21 ohm cable is about 180° out of phase from the incoming microwave signal due to the lower impedance step of the coaxial line.

There is a second location of mismatch that would occur at the junction of the 21 ohm coaxial line and the extended center conductor that forms the antenna. This transition typically will present an impedance parallel to the junction of something between about 50 to 100 ohms when it is loaded into high water content tissues of the body. It is possible to provide the length of the outer conductor of the 21 ohm section so that the reflection of power from the antenna junction is approximately equal in magnitude and of opposite phase to the reflection from the first junction, so that the resultant reflected power is approximately canceled. This provides for greater efficiency. The transition from 21 ohm coaxial cable to the higher parallel impedance at the antenna junction is an impedance step where the reflected voltage does not invert its phase relative to the incident phase since it is a step from lower to higher impedance. Thus, if the outer conductor has an electrical length that is approximately an integral number of half wavelengths in the effective dielectric inside the 21 ohm section of cable, then the phase of the reflection from the first junction will be 180° out of phase from the reflection from the second junction. This causes the two reflected signals to cancel each other as long as their respective voltage amplitude is similar.

The result of this development is that the center conductor is hollow permitting direct access for brachytherapy HDR radiation equipment during the time of a microwave hyperthermia treatment using one or more of these special microwave antenna applicators.

Since the hyperthermia treatment and the brachytherapy treatment could both be completely set-up prior to the initiation of either treatment, this special applicator/catheter would permit a very short sequencing time between the radiation and the hyperthermia treatment. If, for example, the hyperthermia was first, the patient could be up to treatment temperature for 15 to 45 minutes prior to turning the heating power off when the brachytherapy treatment could immediately begin. The brachytherapy treatment may take about 15 minutes to complete, after which the hyperthermia could be resumed for a period of time to further boost the later portion of the radiation treatment.

When the last brachytherapy/radiation treatment is completed, the hyperthermia temperatures could well be increased to higher temperatures that would cause greater direct thermal damage to the tumor. Usually excessive temperatures are avoided in the tumor prior to the final radiation treatment so that the tumor does not become hypoxic and thus radiation resistant. This limitation would not exist during the final hyperthermia treatment of the tumor when the radiation treatments are completed.

Typically brachytherapy HDR equipment uses a metal wire lead attached to the radiation source at the end of the metal wire to be mechanically moved along an inserted catheter device within a cancerous tumor to apply a prescribed radiation dose within the tumor. Prior to the insertion of this radiation source, a metal test wire lead is normally inserted into the catheter to provide assurance that there is no obstruction of the catheter path. The presence of this metal wire being introduced into the hollow center of the active microwave antenna applicator would not be acceptable. Such contact during microwave emission could alter the heating pattern by microwave energy coupling into the wire and being directed into the brachytherapy system. For full independence of the operation of the hyperthermia and the HDR brachytherapy system, these metal wires would need to be replaced by a non-conductor wire material such as plastic. However, by using the metal wire devices in properly time-sequenced insertions during the hyperthermia treatment, it would be possible to provide substantially simultaneous hyperthermia and radiation therapy. This could be accomplished by a coordinated effort to turn off the heating power to a particular antenna when the guide wire or radiation source was to be introduced or scanned. In this way, the radiation therapy wires inside the center conductor of the antenna would not be present when the antenna is transmitting its heating power. Another approach to eliminate the effect of such a metal wire being inserted into the antenna while heating power is on would be to place a microwave blocking device around the connection point to the antenna. Devices such as ferrite beads, microwave chokes, and microwave traps could be used to eliminate or reduce the transfer of microwave fields from the antenna to the metal wires associated with the HDR systems. These techniques cause such microwave energy to be blocked from passing beyond these devices. The ferrite bead approach causes a high impedance to currents in the wire that suppresses these currents. The same mechanism is possible using microwave traps or chokes. Some of these techniques could include forming a metal outer conductor extension along the radiation therapy wire plastic support tube which would form a band-stop coaxial filter for the operating microwave frequency. So although it is not feasible to do actual simultaneous heating with standard HDR systems that have a metal wire without timed coordination of the power on antennas when standard metal wires are in place, the various modifications or adjustments mentioned above in the timing could permit simultaneous heating with radiation therapy. It is typical that even if the heating power is totally turned off to one or more antennas when a particular antenna has the radiation source scanned, such a process may only take about 20 to 30 seconds. In such a short time, the tumor tissues would generally remain at elevated temperatures providing simultaneous treatment.

It is also feasible to utilize radiation sources that are set to the proper radiation length and are inserted into the antenna and left in position for the period of the radiation treatment. Such are typically confined in plastic leader sleeves to permit insertion and removal. One technique is to use Ir-192 radiation source wire or seeds that may remain in place for up to about 3 days.

This new applicator/catheter would permit a special coordination between the brachytherapy treatment and the sequencing of the MW power. If there was coordination between when the test wire and the radiation source were to be introduced into a catheter treatment position, the MW power could be temporarily discontinued during the time the metal wires are inserted into the hollow center conductor of the MW antenna. If sufficient time is permitted for the MW power to continue until another applicator/catheter has a radiation source inserted, then the temperature within the tumor would remain in the therapeutic range during the delivery of the radiation. Typically the dwell time at each 5 mm position for the radiation source is between 2 to 5 seconds depending on the prescribed dose. The typical scan would be about 50 mm in length for each catheter, so the source would only be inserted in the tumor for between 22 to 55 seconds. There would also need to be time planned for removal of the wire as well as running in and out the test wire that precedes each scan. Such coordinated sequencing would permit the radiation treatment from each antenna/catheter to be delivered simultaneously to maximize the effectiveness of a particular radiation dose delivered to the tumor. The lower the radiation dose can be, the lower the acute and long-term toxicity to the patient. Such an approach may enable the radiation delivered by external beam radiation therapy to be reduced or eliminated by brachytherapy combined with interstitial hyperthermia. This may also enable the total dose delivered by brachytherapy to be reduced with a better effectiveness at lower toxicity to the patient. Published studies have shown that there is no increase to long-term toxicity by adding hyperthermia to standard radiation treatments. The only additional toxicity is about a 5% chance that a short-term blister or burn might occur as a result of the hyperthermia treatment. Therefore, the advantages far out-weigh the small short-term risks that can be easily resolved.

A recent article that was published in the International Journal of Radiation Oncology, Biology, and Physics, Vol. 53, No. 1, pp. 6–11, 2002, by Cumberlin and Coleman of the National Cancer Institute is titled "New Directions in Brachytherapy". This article recommended that biological response modifiers for brachytherapy should be explored. Related to this it was stated, "Another example of radiation enhancement is the use of hyperthermia. Although hyperthermia is considerably reduced in its application, the reason for the failure of hyperthermia was largely the inability to heat deep-seated tumors to the target temperature. Given the restriction in the target volume used in brachytherapy, there would now be better options for the local heating of tumors or tumor beds, amenable to brachytherapy."

Microwave interstitial treatments using applicator antennas have been described and clinically used for many years. Turner U.S. Pat. Nos. 4,448,198 and 4,860,752 disclose several such uses.

Efforts to do simultaneous hyperthermia and radiation therapy have been reported in many animal and biological studies. Clinical use of simultaneous hyperthermia and radiation therapy in human cancer treatments have been reported by Robert Meyerson et al. (Meyerson et al. Simultaneous superficial hyperthermia and external radiotherapy: Report of thermal dosimetry and tolerance to treatment, Int. J. of Hyperthermia 1999; 15(7):251–266) where they utilized ultrasound heating equipment configured with a linear accelerator.

Diederich published an article in 1996 (Diederich et al. Direct-coupled interstitial ultrasound applicators for simultaneous thermobrachytherapy: a feasibility study, Int. J. of Hyperthermia 12(3):401–419, 1996) describing how direct-coupled interstitial ultrasound applicators could be configured for simultaneous thermobrachytherapy. This report showed the use of piezoceramic cylinders with a hollow center that permitted the insertion of a brachytherapy source. The use of ultrasound restricted the outer diameter of the inserted device to between 2.4 and 2.6 mm in diameter. This size is larger than most acceptable brachytherapy implant devices that have a maximum diameter of 2.0 mm. In such an application it is necessary to provide an ultrasound-conducting path from the piezoceramic materials to the tissue in order to transfer the ultrasound energy. This reference does not teach the use of microwave antennas that would have a hollow center conductor nor the special requirements to provide proper impedance matching for the microwave energy to efficiently transfer to the tissue.

BRIEF DESCRIPTION OF THE DRAWINGS

In the accompanying drawings, which show the best mode currently contemplated for carrying out the invention.

DETAILED DESCRIPTION OF A PREFERRED EMBODIMENT

The invention includes an apparatus having unique properties that enable both interstitial microwave hyperthermia and interstitial radiation therapy called brachytherapy. This device permits either near simultaneous or simultaneous treatments of these two modalities to gain additional effectiveness in destroying malignant tumors or other localized diseases. The primary requirements for such an integrated approach are that the outer diameter of the inserted device is not too large to safely interstitially insert into a patient and yet have a central hollow tube opening into which a radioactive source can be inserted. The size of a typical radioactive source is 0.9 mm. The typical largest diameter for the inserted devices is 2.0 mm. The novelty of this invention is therefore a method and device that enables the device to provide both interstitial microwave hyperthermia and interstitial radiation therapy while within the limited size requirements stated.

Figure 1:
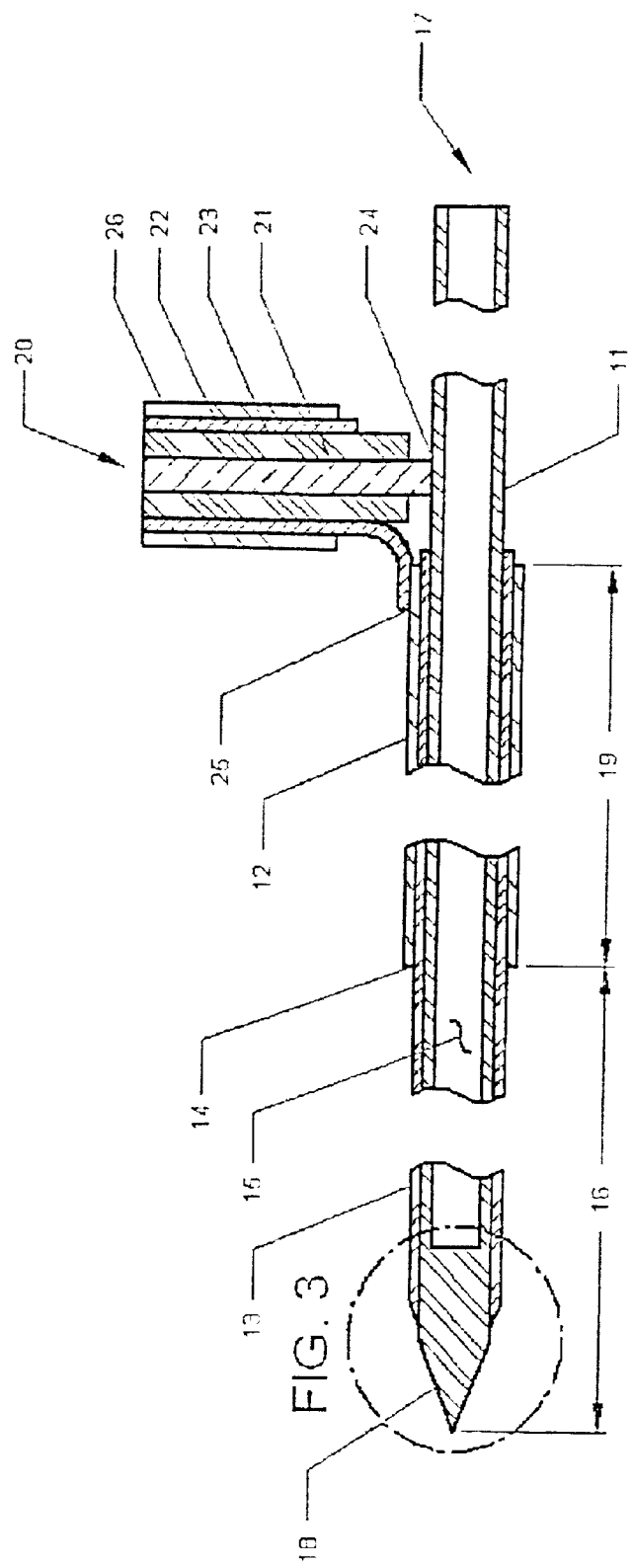
FIG. 1 is a representation of the microwave antenna applicator for hyperthermia that has a coaxial cable section with a center conductor that is hollow to permit the insertion of a radioactive source. It is shown in break-away sections along its length to permit better clarity of the small thickness concentric metal and dielectric tubes that form this coaxial transmission line section.

Referring now to FIG. 1, an invasive microwave antenna applicator 10 is shown with a center conductor metal hollow tube 11. The center conductor tube serves as the center conductor of a coaxial transmission line. The coaxial transmission line is formed by an outer conductor tube 12 which is approximately concentric to the inner conductor tube 11. The two metal conductor tubes 11 and 12 are separated by a dielectric separating tube 13 that preferably fills the space between the two metal tubes. The metal tubes 11 and 12 are of a material that is compatible with direct contact with the body and with sufficiently low electrical resistance to reduce heating of these metals by the microwave currents that flow in the conductors. The preferred material for tubes 11 and 12 is stainless steel or other metals that have a sufficiently conductive outer surface that is biocompatible. The outer surface can be plated, such as with gold plating, to ensure biocompatibility. The dielectric spacing should be of a material that is a good insulator and has low microwave loss such as Teflon, polyethylene, or polystyrene.

The inner conductive tube 11 has a hollow center region 15 that provides a path for the entry of standard radiation therapy radioactive seeds or wires typical in the use of brachytherapy. The standard brachytherapy equipment, not shown, is attached as it would be attached to the normally used catheter for such equipment, in normal manner to the open end 17 of the of the inner conductive tube 11. The brachytherapy radioactive sources are inserted into the hollow tube 15 at open end 17, and can be scanned at any distance along the hollow tube to apply radiation therapy selectively in zones of the diseased tissue. The outer conductor 12 is made shorter in length than the dielectric 13 and the inner conductor 11 by a distance of about 3 cm that is represented by zone length 16. The heating pattern length can be affected and is related to the length of section 16. The tip of the hollow center conductor tube 11 is closed and sharpened at the tip end 18. This allows the antenna applicator to be inserted directly into the tissue with the stiff body and the sharpened tip 18.

The length 19 of the outer conductor 12 is a critical dimension to permit the reflected microwave power supplied at point 24 from a standard coaxial supply cable 20 to be cancelled by the reflected power from the transmitting junction 14. Both at point 24 and at point 14 there is a reflection of microwave power due to the change of transmission line or loading impedance on either side of the points 14 and 24. The length 19 is approximately equal to an integral number of half wavelengths of the coaxial transmission line formed by items 11, 12, and 13. The wavelength cm size in a coaxial line can be determined by the following equation:

$$\text{Wavelength} := \frac{30}{(\text{Frequency MHz} \cdot \sqrt{\varepsilon r})}, \text{cm}$$

If the inner diameter of the outer conductor tube 12 is D, the outer diameter of inner conductor 11 is d, and the effective relative dielectric constant εr of the insulator 13 is typically 2 to 4 (Teflon is 2), the characteristic impedance Zo of the coaxial cable of the antenna applicator is:

$$Zo := 138 \cdot \frac{\log\left(\frac{D}{d}\right)}{\sqrt{\varepsilon r}}$$

Typically, the generator or amplifier system of microwave systems has an output impedance of 50 ohms that is most efficient when connected to a 50 ohm coaxial cable. The 50 ohm coaxial transmission line cable, such as 20, is typically comprised of a center conductor 21, an outer conductive tube 22, and a dielectric insulator 23. Thus, a standard 50 ohm coaxial cable is generally connected from a microwave power source to the point 24 for the center conductor and point 25 for the outer conductor.

EXAMPLE

The typical parallel equivalent loading impedance of the tip region 16 of the applicator 10 ranges from about 50 to 100 ohms. This permits the proper selection of the conductor diameters and the length of the outer conductor 12 to obtain an efficient microwave energy transfer to the microwave transmitting section 16 of the antenna. The radiation therapy can be directed by a brachytherapy radiation source in center hollow area 15 of the applicator through the materials of 11, 12, and 13 with little alteration from the radiation applied by the normal brachytherapy catheter. The radiation therapy dose is controlled by the brachytherapy equipment operated by the medical staff. The typical heating region of the applicator is constrained to a diameter of about 3 cm and a length of about 5 cm for an operating frequency of 915 MHz with length 16 equal to about 3 cm. In this example, the outer conductor 12 is preferred to be one full wavelength long (that is 23 cm for Teflon filled dielectric) at 915 MHz. In this case, the dielectric tube insulator 13 is Teflon with a relative dielectric constant of about 2. In this example, the diameter d is 1.07 mm and the diameter D is 1.78 mm. Typically brachytherapy radiation sources have a diameter of 0.9 mm.

Figure 2:
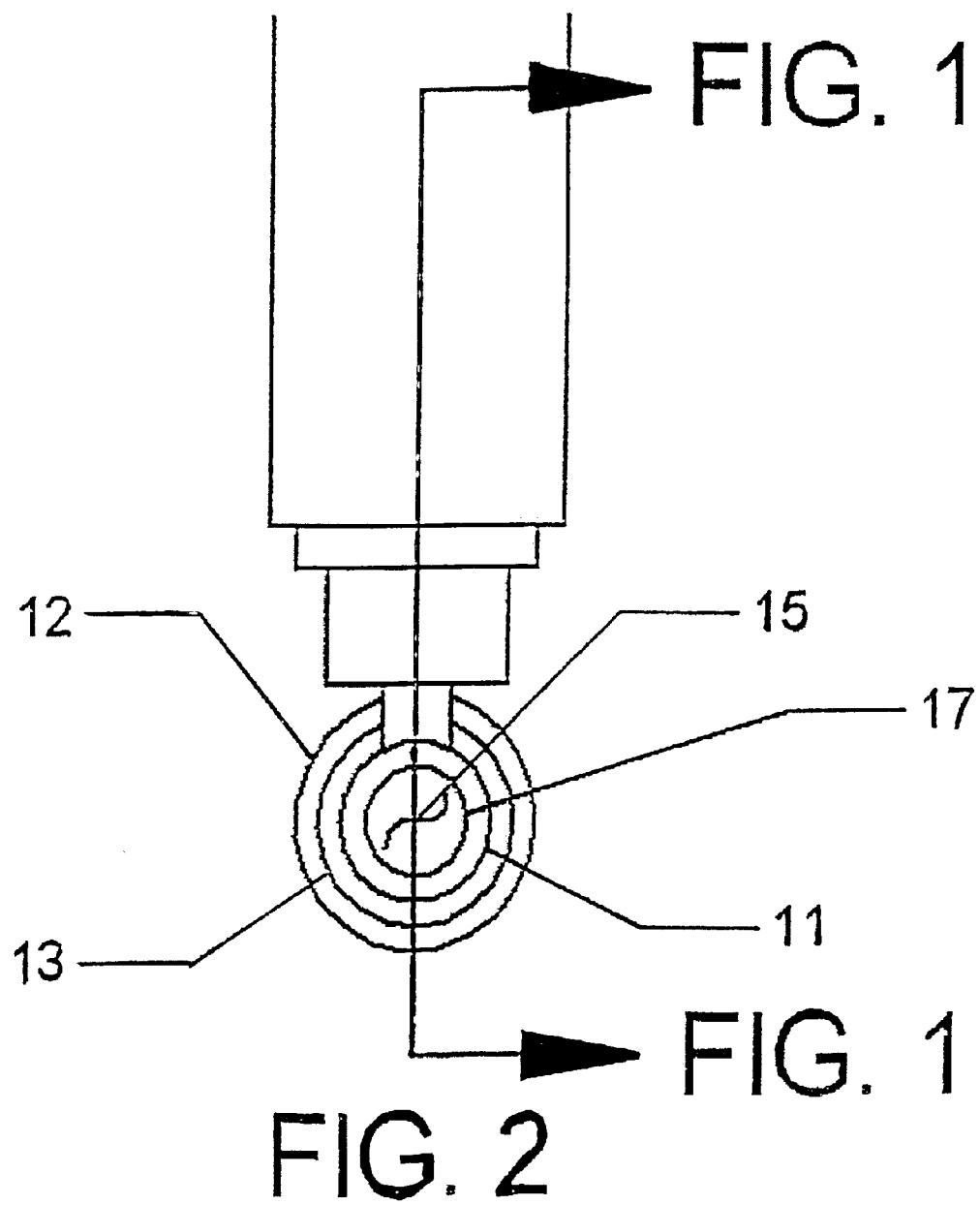
FIG. 2 shows an end view of the microwave antenna applicator showing the hollow opening that permits the insertion of a radioactive source for radiation therapy.

In FIG. 2 shows the open end 17 of the hollow applicator antenna that enables the insertion of a standard radioactive source for radiation therapy into the hollow tube center 15. Item 11 shows the tubular center conductor of the coaxial microwave transmission line. Item 12 shows the tubular metal outer conductor of the coaxial transmission line. Item 13 shows the dielectric tube that separates the center and outer conductor tubes.

Figure 3:
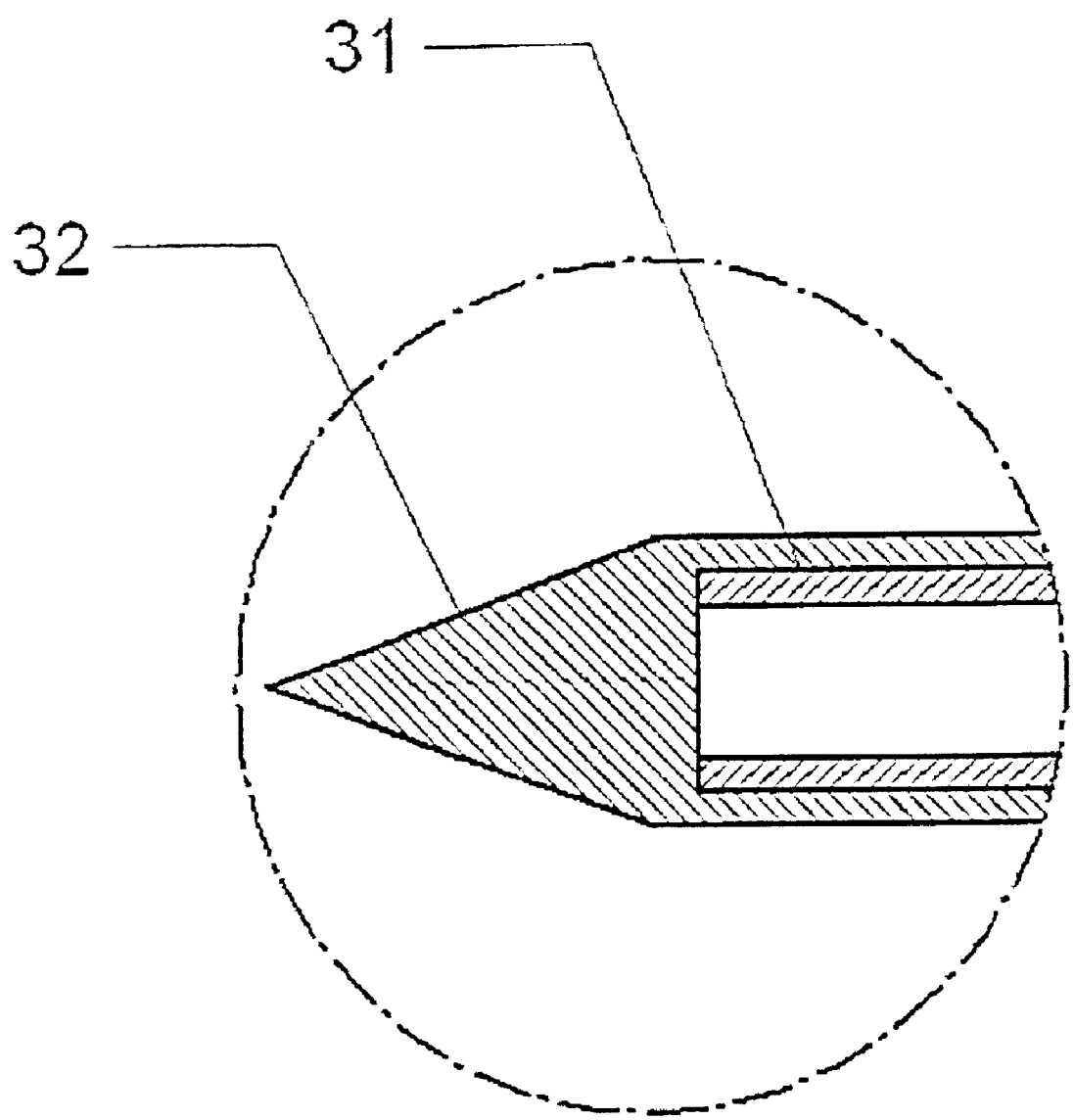
FIG. 3 shows an alternate form tip where rather than a metal cutting tip, a sharpened dielectric such as plastic is used for the cutting tip.

FIG. 3 shows an alternative design of the applicator where the dielectric tube, here shown as 32, is sharpened to form the sharpened applicator tip. The inner metal conductive tube 31 is constrained and embedded within the dielectric tube. Note that inner metal tube 31 is shown as an open ended metal tube, but it can also be a flattened blunt end that is closed to better support the plastic sharpened tip.

Figure 4:
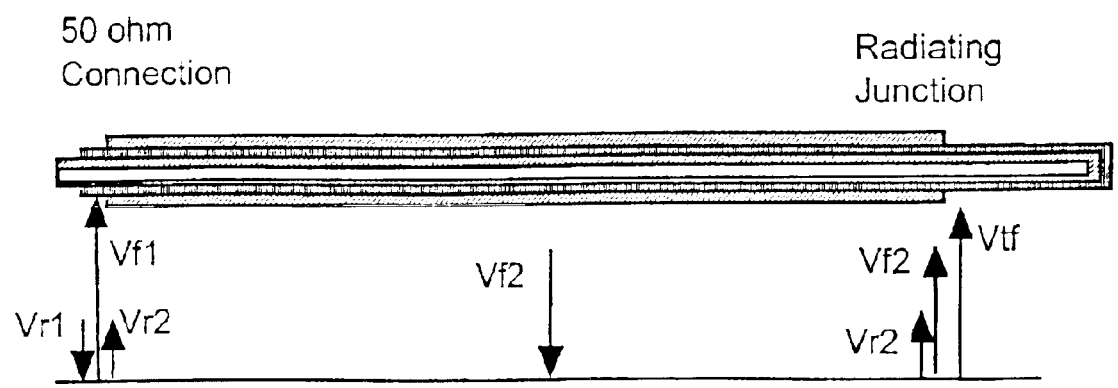
FIG. 4 shows a diagram representing the forward directed voltage vector fields Vf1, Vf2, and Vtf along with the reflected voltage vector fields represented along the antenna/applicator representation.

FIG. 4 is a diagram representing the voltage vectors of the microwave field as they would exist along the representation of the antenna/applicator. The vector Vf1 represents the input microwave voltage vector at the input (typically 50 ohms). The Vr1 represents the reflected voltage vector at the transition point of the 50 ohm input to the lower impedance transmission line. Note that Vr1 is shown to align with a 180 degree phase inversion where the pointing vector would point in an opposite direction to the incoming voltage vector. Therefore, the difference between these two vectors would result in a lower voltage vector continuing through the lower impedance transmission line that is represented by Vf2. Note that the diagram shows that Vf2 in the midway point along the low impedance coaxial section is also inverted. This represents the condition that would exist if the coaxial line length was a full wavelength long. In such a case, the Vf2 would have gone through a phase change of 180° so its relative voltage vector would be pointing in an opposite direction as represented by the diagram. However, as this Vf2 would reach the radiating junction, the additional travel distance along the coaxial cable would cause the Vf2 vector to be further changed by 180°. Thus, the vector Vf2 that is present at the radiating junction is again shown pointing in the same direction as the initial Vf1. The reflection Vr2 that would come from the impedance transition from the lower impedance coaxial section to a higher effective loading impedance of the radiating antenna would not be inverted relative to the incoming Vf2. So the resultant voltage vector that would continue beyond the radiating junction would be the Vtf as shown in the diagram. Note that at the 50 ohm connection-junction point, Vr2 is shown with the same magnitude and an opposite phase alignment to the Vr1 voltage vector. This results in the cancellation of reflected power to the 50 ohm source cable and generator system providing high microwave energy efficiency and transfer from the power source to the radiating junction. Thus, the lower impedance coaxial section permits the much larger center conductor tube diameter to provide a large opening while still maintaining high efficiency.

It should also be recognized that the hollow applicator could be utilized in the same way if the source impedance of the system cable were a lower impedance than that of the low impedance antenna coaxial section. However, in such a case the length of the outer conductor would be either lengthened or shortened to change the one-way phase delay of the outer conductor section by 90 degrees, i.e., one quarter wavelength. This would require an unconventional source impedance for connection to the antenna, but would still provide for the low impedance needed for the hollow inserted section.

Although several embodiments of the invention have been described, it will be apparent to a person skilled in the art that various modifications of the details of the construction that is shown and described may be made without departing from the broader inventive concepts disclosed herein and comprehended by the claims that follow.

What is claimed is:

1. A microwave hyperthermia antenna applicator for heating local regions of tissue within a living body, comprising:
   (a) a hollow central conductor having a length and sufficient in size to permit the insertion of radiation therapy sources;
   (b) an outer conductor having a length and positioned substantially coaxially with the central conductor along a portion of the length of the hollow central conductor to form a coaxial section of the applicator having impedance lower than the impedance of a coaxial source cable that would connect the applicator to a source of microwave power, the inner conductor extending beyond the outer conductor to form a microwave radiating section having a higher impedance than the coaxial section; and (c) wherein the length of the coaxial section is approximately equal to an integral number of half wavelengths of microwave energy of a frequency expected to be applied to the applicator by the coaxial source cable, such hat the impedance matching for the connection point of the microwave source cable to the applicator is substantially impedance matched for efficient transfer of microwave power from the source cable to the tissue surrounding the microwave radiating section.

2. A microwave hyperthermia antenna applicator according to claim 1, additionally including a dielectric material positioned between the inner conductor and the outer conductor.

3. A microwave hyperthermia antenna applicator according to claim 2, wherein the microwave radiating section includes a sharpened applicator tip, and wherein the sharpened tip is a sharpened metal tip.

4. A microwave hyperthermia antenna applicator according to claim 3, wherein the sharpened metal tip is connected to the center conductor.

5. A microwave hyperthermia antenna applicator according to claim 4, wherein the sharpened metal tip is formed as the forward end of the center conductor.

6. A microwave hyperthermia antenna applicator according to claim 2, wherein the microwave radiating section includes a sharpened applicator tip, and wherein the sharpened tip is a sharpened dielectric tip.

7. A microwave hyperthermia antenna applicator according to claim 6, wherein the sharpened dielectric tip is connected to the dielectric material positioned between the inner conductor and the outer conductor.

8. A microwave hyperthermia antenna applicator according to claim 7, wherein the sharpened dielectric tip is formed as the forward end of the dielectric material positioned between the inner conductor and the outer conductor.

9. A microwave hyperthermia antenna applicator according to claim 1, wherein the microwave radiating section includes a sharpened applicator tip, and wherein the sharpened tip is a sharpened metal tip.

10. A microwave hyperthermia antenna applicator according to claim 9, wherein the sharpened metal tip is connected to the center conductor.

11. A microwave hyperthermia antenna applicator according to claim 10, wherein the sharpened metal tip is formed as the forward end of the center conductor.

12. A microwave hyperthermia antenna applicator according to claim 1, additionally including the coaxial source cable having a center source conductor and an outside source conductor, and wherein the center source conductor is connected to the center conductor and the outer source conductor is connected to the outer conductor, said coaxial source conductor adapted to be connected to a source of microwave power.

13. A microwave hyperthermia antenna applicator according to claim 12, wherein the hollow center conductor opens to outside the conductor through an end opening adapted to be connected to brachytherapy equipment.

14. A microwave hyperthermia antenna applicator according to claim 1, wherein the hollow center conductor opens to outside the conductor through an end opening adapted to be connected to brachytherapy equipment.

15. A microwave hyperthermia antenna applicator according to claim 1, wherein the hollow central conductor has an inside diameter sufficient to receive therein a radiation therapy source having a diameter up to 0.9 mm, and the outer conductor has an outer diameter of no more than 2 mm.

16. A microwave hyperthermia antenna applicator according to claim 15, wherein the hollow central conductor has an inside diameter of between 0.927 mm and 0.978 mm, and the outer conductor has an outer diameter o between 1.816 mm and 1.842 mm.

17. A microwave hyperthermia antenna applicator for heating local regions of tissue within a living body, comprising:

(a) a hollow central conductor having a length and sufficient in size to permit the insertion of radiation therapy sources;

(b) an outer conductor having a length and positioned substantially coaxially with the central conductor along a portion of the length of the hollow central conductor to form a coaxial section of the applicator having an impedance different than the impedance of a coaxial source cable that would connect the applicator to a source of microwave power, the inner conductor extending beyond the outer conductor to form a microwave radiating section having a different impedance than the coaxial section; and (c) wherein the length of the coaxial section is selected such that the impedance matching for the connection point of the microwave source cable to the applicator is substantially impedance matched for efficient transfer of microwave power from the source cable to the tissue surrounding the microwave radiating section.

18. A method of combining microwave hyperthermia treatment and brachytherapy radiation treatment to body tissue of a patient to be treated, comprising the steps of:

obtaining a microwave hyperthermia applicator comprising:

(a) a hollow central conductor having a length and sufficient in size to permit the insertion of radiation therapy sources;

(b) a microwave source cable adapted to be connected to a source of microwave power and having a central source conductor and an outer source conductor;

(c) an outer conductor having a length and positioned substantially coaxially with the central conductor along a portion of the length of the hollow central conductor to form a coaxial section of the applicator having an impedance lower than the impedance of the coaxial source cable, the inner conductor extending beyond the outer conductor to form a microwave radiating section having a higher impedance than the coaxial section, the center source conductor being connected to the center conductor and the outer source conductor being connected to the outer conductor; and (d) wherein the length of the coaxial section is approximately equal to an integral number of half wavelengths of microwave energy of a frequency expected to be applied to the applicator by the coaxial source cable, such that the impedance matching for the connection point of the microwave source cable to the applicator is substantially impedance matched for efficient transfer of microwave power from the source cable to the tissue surrounding the microwave radiating section;

inserting the applicator into the body tissue to be treated;

connecting the source cable to a source of microwave power to supply such microwave power to the applicator;

connecting the applicator to a brachytherapy radiation source; and selectively supplying microwave power to the applicator and a brachytherapy radiation source to the applicator at predetermined, coordinated times to provide coordinated hyperthermia and brachytherpy treatments.

19. A method of combining microwave hyperthermia treatment and brachytherapy radiation treatment according to claim 18, wherein the step of obtaining a microwave hyperthermia applicator is the step of obtaining a plurality of such applicators, and the step of inserting the applicator into the body tissue to be treated is the step of inserting the plurality of applicators as an array into the body tissue to be treated.

20. A method of combining microwave hyperthermia treatment and brachytherapy radiation treatment according to claim 19, wherein the plurality of applicators are all supplied with microwave power simultaneously or with brachytherapy radiation sources simultaneously to provide simultaneous hyperthermia treatment or simultaneous brachytherapy radiation treatment.

21. A method of combining microwave hyperthermia treatment and brachytherapy radiation treatment according to claim 20, wherein the coordinated times are separate times separated by preset time intervals.

22. A method of combining microwave hyperthermia treatment and brachytherapy radiation treatment according to claim 19, wherein selected individual applicators of the plurality of applicators are supplied with microwave power while other selected individual applicators of the plurality of applicators are supplied with brachytherapy radiation sources to provide simultaneous hyperthermia treatment and brachytherapy radiation treatment.

23. A method of combining microwave hyperthermia treatment and brachytherapy radiation treatment according to claim 19, wherein the step of connecting the applicator to a brachytherapy radiation source is the step of connecting the applicator to brachytherapy equipment, and additionally including the step of blocking the flow of microwave power from the applicator into the brachytherapy equipment when both microwave hyperthermia treatment and brachytherapy radiation treatment occur simultaneously for the same applicator.

24. A method of combining microwave hyperthermia treatment and brachytherapy radiation treatment according to claim 18, wherein the step of connecting the applicator to a brachytherapy radiation source is the step of connecting the applicator to brachytherapy equipment, and additionally including the step of blocking the flow of microwave power from the applicator into the brachytherapy equipment when both microwave hyperthermia treatment and brachytherapy radiation treatment occur simultaneously.

25. A method of combining microwave hyperthermia treatment and brachytherapy radiation treatment according to claim 18, wherein the coordinated times are separate times separated by preset time intervals.

26. A microwave hyperthermia antenna applicator according to claim 18, wherein the hollow central conductor has an inside diameter sufficient to receive therein a radiation therapy source having a diameter up to 0.9 mm, and the outer conductor has an outer diameter of no more than 2 mm.

27. A microwave hyperthermia antenna applicator according to claim 26, wherein the hollow central conductor has an inside diameter of between 0.927 mm and 0.978 mm, and the outer conductor has an outer diameter of between 1.816 mm and 1.842 mm.

* * * * *